United States Patent
MacNeil

(10) Patent No.: US 7,383,649 B2
(45) Date of Patent: *Jun. 10, 2008

(54) VEHICLE LICENSE PLATE FRAME

(76) Inventor: David F. MacNeil, 2435 Wisconsin St., Downers Grove, IL (US) 60515

( * ) Notice: Subject to any disclaimer, the term of this patent is extended or adjusted under 35 U.S.C. 154(b) by 0 days.

This patent is subject to a terminal disclaimer.

(21) Appl. No.: 11/383,026

(22) Filed: May 12, 2006

(65) Prior Publication Data

US 2006/0207131 A1 Sep. 21, 2006

Related U.S. Application Data

(63) Continuation of application No. 10/763,645, filed on Jan. 22, 2004, which is a continuation of application No. 10/151,361, filed on May 17, 2002, now Pat. No. 6,760,986.

(51) Int. Cl.
G09F 7/00 (2006.01)

(52) U.S. Cl. .............. 40/200; 40/209; 40/718; 40/578; 277/613; 277/637; 277/641; 277/642; 277/643

(58) Field of Classification Search .......... 40/209, 40/200, 718, 207; 277/613, 637, 641
See application file for complete search history.

(56) References Cited

U.S. PATENT DOCUMENTS 1,363,409 A * 12/1920 Gulde .................... 40/643
1,664,302 A * 3/1928 Garis et al. .............. 40/205
2,130,090 A 9/1938 Imhofe
2,144,261 A 1/1939 Johnston
3,050,654 A 8/1962 Toulon
3,231,288 A 1/1966 Hensien
3,445,151 A * 5/1969 Stefanakis .............. 359/514
3,894,371 A 7/1975 Yamaha
3,895,987 A * 7/1975 Loreck .................. 156/223
3,983,650 A 10/1976 Payson
4,123,071 A 10/1978 Yamamoto
4,182,062 A * 1/1980 Krokos et al. ........... 40/209
4,183,160 A * 1/1980 Brodersen .............. 40/718
4,308,965 A * 1/1982 Dutt ..................... 215/345
4,331,249 A 5/1982 Banich, Sr.
4,379,512 A 4/1983 Ohmi et al.
4,478,020 A 10/1984 Jackson
4,546,986 A 10/1985 Roselli (Continued)

FOREIGN PATENT DOCUMENTS

CH 659905 A5 * 2/1987

OTHER PUBLICATIONS

Screen print of Internet website: www.macneilauto.com/store/frames.html, downloaded Sep. 4, 2002.

*Primary Examiner*—Robert J. Sandy
*Assistant Examiner*—Marcus Menezes
(74) *Attorney, Agent, or Firm*—Momkus McCluskey, LLC; Jefferson Perkins

(57) ABSTRACT

A transparent vehicle license plate frame has an elastomeric gasket. The frame includes a periphery and an inner side for disposal adjacent to a license plate. The elastomeric gasket is disposed on the inner side near the periphery of the frame and is injection-molded into an annular frame channel.

8 Claims, 4 Drawing Sheets

U.S. PATENT DOCUMENTS

| | | |
|---|---|---|
| 4,813,167 A | 3/1989 | Means |
| 4,850,125 A | 7/1989 | Green |
| 4,891,895 A * | 1/1990 | DeLaquil, Jr. ............... 40/209 |
| 5,205,059 A * | 4/1993 | Doll ........................... 40/718 |
| 5,226,251 A * | 7/1993 | Webb .......................... 40/508 |
| 5,255,168 A | 10/1993 | Stevens |
| 5,307,574 A | 5/1994 | Huff, Jr. |
| 5,400,533 A * | 3/1995 | Cruse .......................... 40/718 |
| 5,440,849 A * | 8/1995 | Agrawal et al. ............. 52/393 |
| 5,623,776 A * | 4/1997 | Lucier ......................... 40/209 |
| 5,901,482 A * | 5/1999 | Sawyer et al. ................ 40/308 |
| 5,918,393 A | 7/1999 | Martell |
| 5,947,311 A | 9/1999 | Gregory |
| 5,950,339 A * | 9/1999 | Lucier ......................... 40/209 |
| 6,202,872 B1 | 3/2001 | Smeyak et al. |
| 6,262,807 B1 * | 7/2001 | Pleotis ....................... 358/1.2 |
| 6,302,782 B1 | 10/2001 | Yip |
| 6,385,876 B1 * | 5/2002 | Mc Kenzie ................. 40/201 |
| 6,688,030 B2 * | 2/2004 | Vihos .......................... 40/718 |

\* cited by examiner

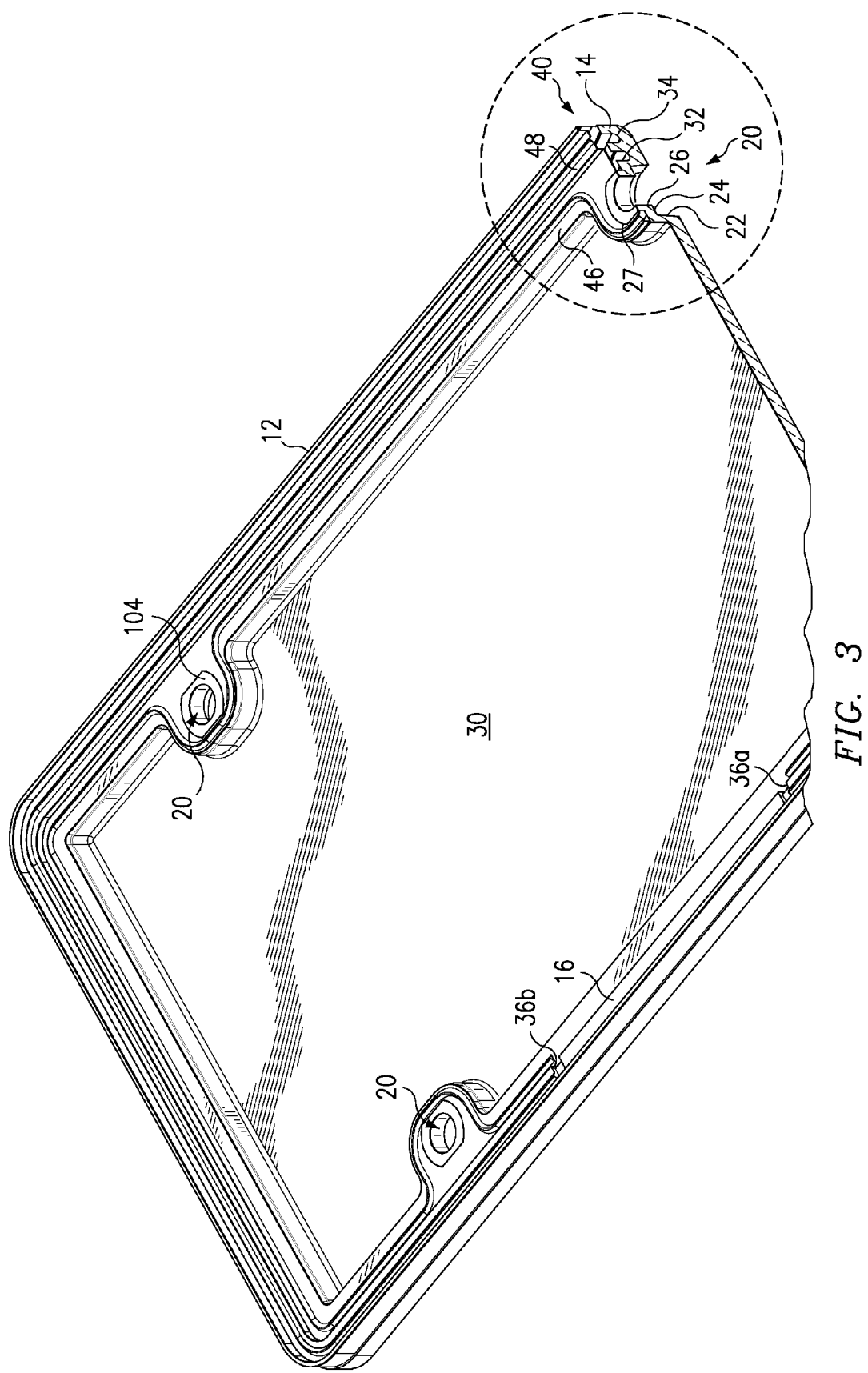

VEHICLE LICENSE PLATE FRAME

CROSS REFERENCE TO RELATED APPLICATIONS

This application is a continuation of copending U.S. patent application Ser. No. 10/763,745 filed Jan. 23, 2004, which in turn is a continuation of U.S. patent application Ser. No. 10/151,361 filed May 17, 2002, now U.S. Pat. No. 6,760,986. The disclosures of these applications are fully incorporated by reference herein.

TECHNICAL FIELD OF THE INVENTION

The present invention relates in general to a protective covering, and more particularly to a license plate cover for protecting a license plate from rain, slush, salt, debris and other adverse elements found in the highway environment.

BACKGROUND OF THE INVENTION

When a vehicle is driven or parked outside, the vehicle license plate is exposed to chemical, abrasive and actinic attack from causes such as water; aqueous solutions of harsh chemicals, notably road salt; organics such as road tar; abrasive particulates, typically silicates; macroscopic debris such as pebbles and insects; ozone; and solar and heat radiation, the former of which includes aging ultraviolet radiation. Optimally, the outside surface of a highway vehicle must withstand combinations of these adverse environmental actors, even as the vehicle is moving through the air at 65 mph or greater. The environment near the highway surface can be particularly unforgiving.

Government-issued vehicle identification plates may not be as weather-impervious as the rest of the vehicle, and without protection one often sees license plates which have been sand-blasted, etched, mangled and sun-faded on otherwise presentable vehicles. Further, the fasteners that attach the license plate to the vehicle may rust. As a result, the license plate may become difficult to remove.

License plate covers have been used to protect license plates from these damaging environmental factors. Generally, conventional license plate covers do not have a seal positioned around the rim of the cover to protect the license plate. However, a license plate cover made by Altec includes as a separate component, a circumferential gasket for positioning around the edge of the cover. The Altec license plate cover also includes, as separate pieces, compression-limiting sleeve inserts used in each of the screw holes in order to ensure that the screws do not overcompress the gasket and fracture the frame member. Prior license plate covers also include rubber mounting caps that are used to cover the fasteners that attach the license plate and license plate cover to the vehicle. Prior license plate covers, however, fail to provide an adequate seal that prevents unwanted elements from damaging the license plate or fasteners. As a result, a need exists to provide an improved license plate cover that adequately seals a license plate from various environmental elements.

License plate covers have also been provided with circumferential bands or borders of color to complement the vehicle basic or trim color. Such a border has been painted on the external side of the license plate cover, where it is subject to gradual removal by abrasion, or has been painted on the interior side where it may be viewed through the transparent cover. While painting a color band on the interior side is an improvement, it still represents a separate manufacturing and material cost increment over covers without such a color band or border or which use no such paint or coating.

SUMMARY OF THE INVENTION

According to one aspect of the invention, a vehicle license plate frame has an elongated thermoplastic elastomeric gasket injection-molded into an annular channel formed on the inner side of the frame body. The frame body is formed of a relatively tough, rigid, weather-resistant material, such as an acrylic resin.

In one embodiment, the frame body is transparent and the gasket is colored. The close adherence of the injection-molded thermoplastic elastomeric gasket material to the inner side of the frame body, including the bottom and sides of the channel, without refraction-causing air gaps, creates a vivid band of color around the plate when viewed from the outer side. While a consumer-selectable band of color is thus perfectly transmitted through the transparent frame to be visible from the outer side of the frame, the colored component is not easily attacked by the elements, and therefore persists in like-new condition. The separate step and material cost of painting a color band on the cover is avoided.

In a further aspect of the invention, a vehicle license plate frame has a body which is provided with a plurality of mounting fastener holes. Each hole is bounded by a sidewall of relatively rigid material, formed to be integral with the frame body, and which extends continuously from the outer side of the frame to its inner side. An elastomeric gasket is disposed around the periphery of the frame and to closely laterally surround the holes. This gasket forms a generally planar receiving surface which faces inwardly toward the license plate. Each sidewall extends inwardly until its inner end is substantially coplanar with the general receiving surface of the gasket. This prevents cracking of the frame due to overcompression of the gasket by the fasteners.

BRIEF DESCRIPTION OF THE DRAWINGS

Further aspects of the invention and their advantages may be discerned from the following description when taken in conjunction with the drawings, in which like characters identify like parts and in which:

FIG. 3 is a partial rear isometric view of the license plate cover illustrated in FIG. 1;

DETAILED DESCRIPTION

Figure 1:
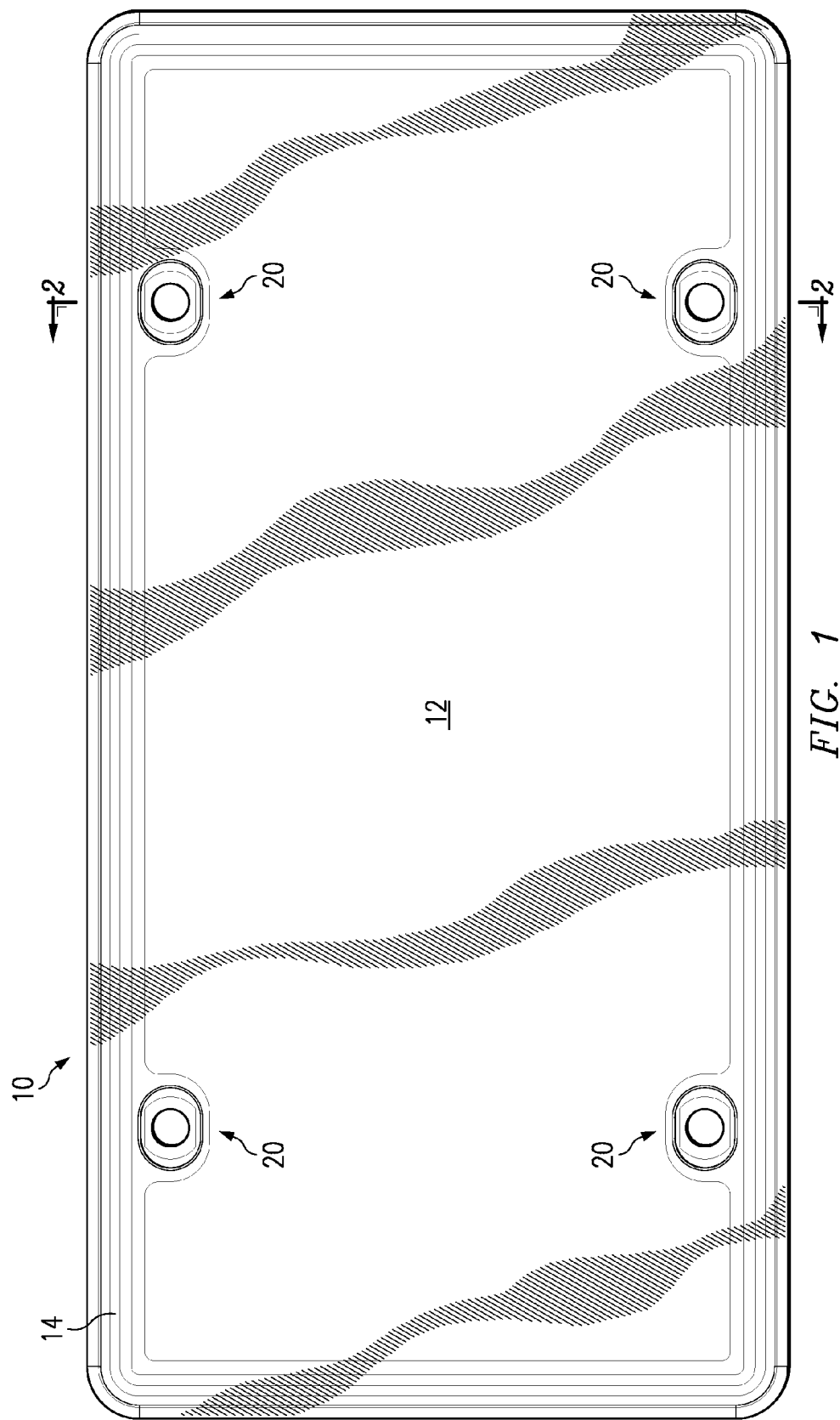
FIG. 1 is a front plan view of the license plate cover of the present invention.
Figure 5:
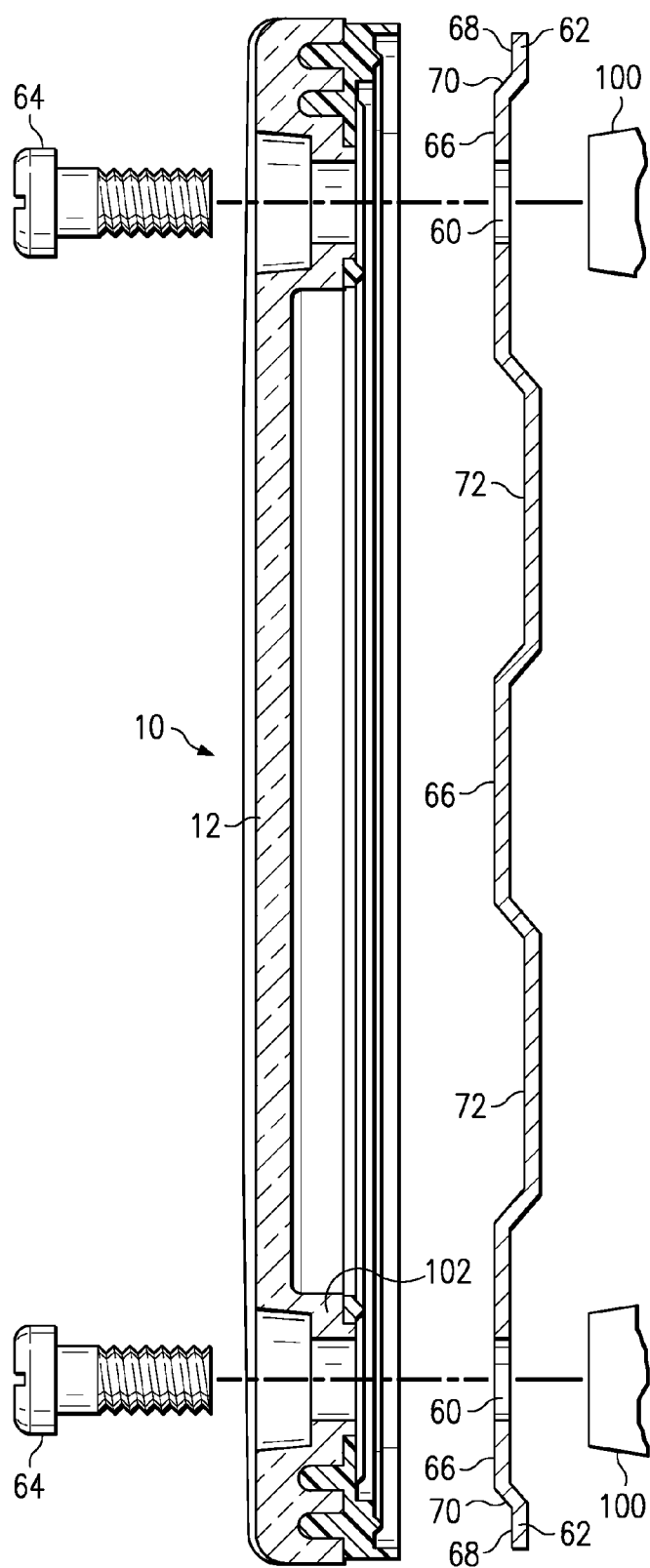
FIG. 5 is an exploded side view of the license plate cover of FIG. 1 showing installation on a license plate.

In FIG. 1, the front license plate cover indicated generally at 10 is rectangular and is sized to overlap a vehicle license plate (see FIG. 5). The license plate cover 10 includes a frame 12 with a periphery 14 and a gasket 40 formed from a natural or synthetic elastomer best seen in FIGS. 2, 3 and 4. The gasket 40 is positioned in the inner side 30 of the frame 12 along the periphery 14 of the frame 12. The frame 12 is transparent and formed from a tough plastic material, such as an acrylic or polycarbonate.

The frame 12 includes mounting holes 20, typically four in number, that align with the holes in a conventional license plate and a vehicle license plate mounting bracket. The mounting holes 20 are configured to receive a fastener 64, such as a bolt, to secure the license plate cover 10 to a vehicle (see FIG. 5). Each mounting hole 20 includes a stepped or double level opening (see FIGS. 2 and 3).

Figure 2:
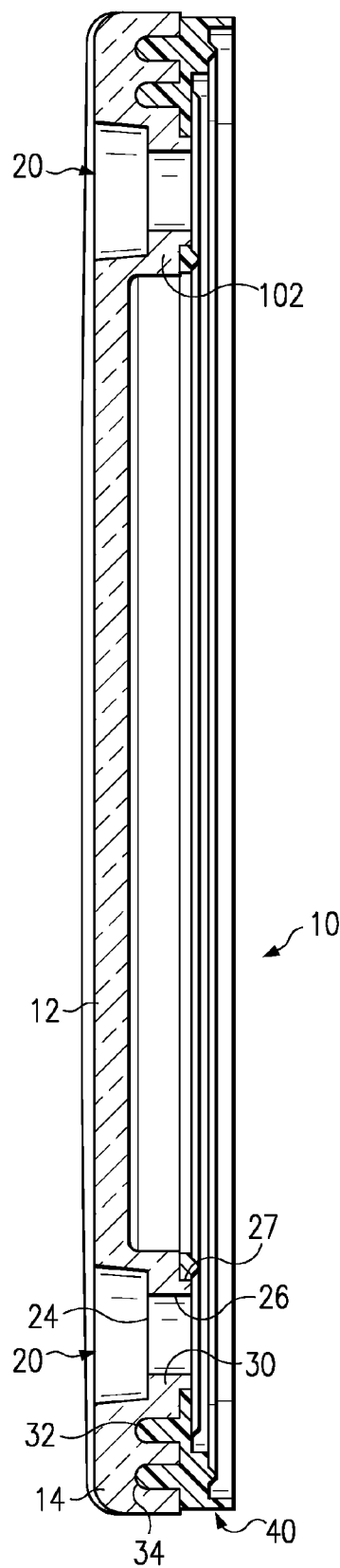
FIG. 2 is a cross sectional side view taken substantially along line 2-2 of FIG. 1.
Figure 4:
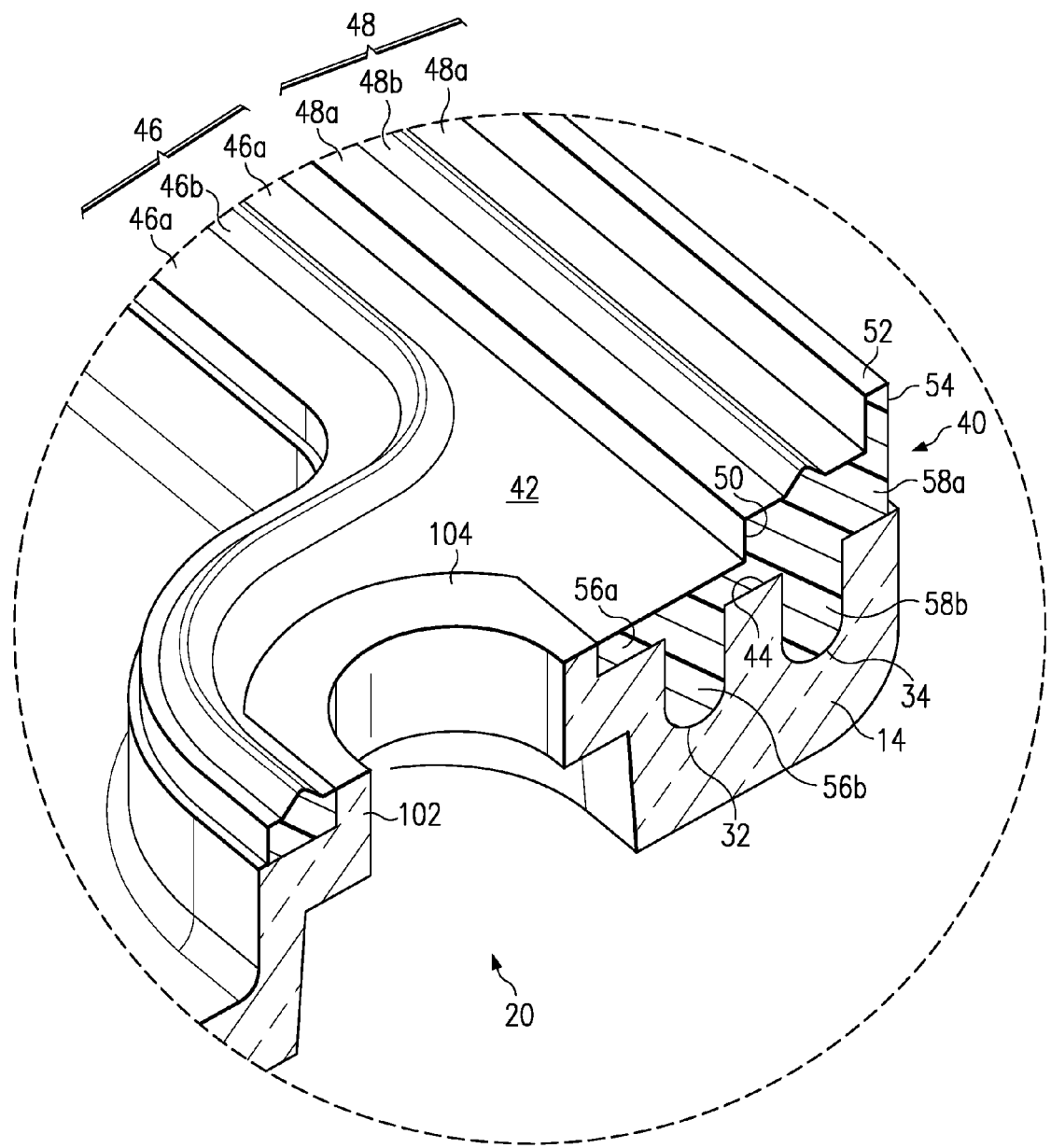
FIG. 4 is a sectional detail of the gasket in the frame of the license plate cover illustrated in FIG. 1.

FIGS. 2, 3 and 4 illustrate the inner side 30 of the frame 12. The inner side 30 of the frame 12 includes two channels 32 and 34 located near the periphery 14 of the frame 12. An elastomer is injection molded into the channels 32 and 34 to form the gasket 40. As shown in FIG. 3, the gasket 40 also surrounds the mounting holes 20 thereby supplying a peripheral seal to the mounting holes 20. In a preferred embodiment, the frame 12 and the gasket 40 are formed in the same mold by a two-shot injection molding process.

The channels 32 and 34 extend around all or a substantial portion of the periphery 14 of the frame 12.

FIGS. 2, 3 and 4 also illustrate the stepped or double level mounting holes 20 that are positioned in the frame 12. The first level 22 of the mounting hole 20 has an oblong shape with a varying width that narrows as it approaches the inner side 30 of the frame 12. The first level 22 and second level 26 meet at step 24. The step 24 is located at approximately the middle of the depth of the frame 12. The second level 26 of the mounting hole 20 has a circular shape and is configured to receive the shank or body of a fastener 64. The second level 26 of mounting hole 24 is defined by an enclosing sidewall 102 of relatively incompressible, hard plastic material which extends from the step 24 to a surface 104 which is substantially coplanar with general interior gasket surface 46a (described below). The enclosing sidewall 102 acts as a compression delimiter; the mounting screws will be able to compress only upstanding gasket ribs 46b, 48b, but not the remainder of the gasket body. Enclosing sidewalls 102 prevent the fasteners from overcompressing the gasket and fracturing the frame of the license plate cover.

After the fastener 64 (See FIG. 5) is installed, mounting hole 20 is filled with the fastener head and a rubber mounting cap. The mounting cap (not shown) surrounds and seals the fastener so as to protect it from environmental attack. The shape of the openings of each level of the mounting holes may also vary; for example, the first level opening could also be circular.

FIG. 4 is a detail of a preferred form of a gasket 40 that is installed in the license plate cover of the present invention. The gasket 40 is formed from an elastomer, such as saniprene, or another organic rubber with an ultraviolet inhibitor. A suitable elastomer is Multi-Flex® TEA from Multibase. When the gasket is injection molded into the channels 32 and 34 of the transparent license plate cover frame, the front of the license plate cover displays the color of the gasket, which can be chosen to be clear or a transparent color. As the gasket is injection molded into the frame, the liquid elastomer adheres to or "wets" the surface of the channels and the frame such that a complete molecular interface is formed between the gasket and the frame. Thus, the gasket completely contacts the inner surface of the channels and the frame. Since there are no air gaps, there will be no refraction or light scattering at the gasket/cover interface, and there will be virtually complete light transmission through the frame member from the gasket surface. As a result, the license plate cover as viewed from the outside has a consistently colored border of undiminished hue.

The gasket 40 may be colored by a variety of colors, including clear or transparent, so that the user may select a license plate cover that matches (or pleasingly contrasts with) the color of his or her vehicle. Preferably, the mounting caps are also colored to match the color of the gasket 40. Because the colored piece is disposed behind the tough, transparent frame 12, it will not be worn or abraded, will be less subject to chemical attack and therefore will retain its initial brightness longer. The gasket 40 thus provides a colored band without the additional step of applying paint to either the inside or the outside of frame member 12.

The gasket 40 includes a license plate receiving surface 42 and an opposed frame mounting or retaining surface 44. The receiving surface 42 includes a first section 46 and a second section 48. The first section 46 and the second section 48 are separated by a step 50. In a preferred embodiment, the step 50 is approximately 0.05 inches to 0.10 inches high. As a result, the second section 48 is positioned in a plane above that of the first section 46 as illustrated in FIGS. 3 and 4. In use, the step 50 is disposed adjacent to a license plate when the license plate cover is installed over the license plate on a vehicle (See FIG. 5).

Each receiving surface section 46 and 48 includes a substantially flat surface section 46a and 48a, respectively. Each flat surface section 46a and 48a also includes an elongated upstanding compression rib 46b or 48b. The compression ribs 46b and 48b protrude inwardly from the rear of the frame to intentionally different heights so that the compression ribs 46b and 48b are disposed to be adjacent respectively to a raised central area 66 and a depressed peripheral area 68 of a license plate (FIG. 5). The inwardmost surface of compression rib 48b is oriented in a plane inward relative to an inwardmost surface of compression rib 46b. Compression rib 46b is centered over the channel 32 except for the area under the mounting holes. At each mounting hole, the compression rib 46b extends from its location above channel 32 laterally inwardly around the outer periphery of the mounting hole. At the opposite side of the mounting hole, the compression rib 46b resumes its position over the channel 32. The compression rib 48b is centered over the channel 34. As best shown in FIGS. 4 and 5, the routing of inner compression rib 46b to the interior of the mounting holes provides a further anticorrosion barrier for the fasteners.

As best seen in FIG. 3, the peripheral compression ribs 46b, 48b seal most of the periphery of the frame, but not all of it. A gap 16 and drain channels 36a and 36b are intentionally left open on the bottom center of the cover. This is to permit air pressure equalization when the vehicle changes altitude, and provides a gravity drain for any moisture which may have found its way under the cover 10.

The receiving surface 42 of the gasket 40 also includes a raised rim 52 which forms the outer edge 54 of the gasket 40. The raised rim 52 is in a plane inward that of the compression ribs 46b and 48b. The raised rim is located around the periphery of the gasket 40. Thus, the raised rim 52 fits over and around an outer edge of the license plate when installed over the license plate of a vehicle.

The compression ribs 46b and 48b have a triangular or inverted V-shape. The sections of the compression ribs 46b and 48b, however, could be formed from other shapes, such as a circle or an ellipse. In addition to the raised rim 52, the compression ribs 46b and 48b provide a barrier to the environmental elements, including rain and slush.

The mounting surface 44 of the gasket 40 closely (and preferably, exactly) conforms to the shape of the channels 32 and 34 and the inner side 30 of the frame 12. In the preferred embodiment, this is accomplished automatically by using a two-step injection molding process, in which the channels 32 and 34 are formed in a first step and are filled with a fluid elastomer in a second step. Thus, the mounting surface 44 surrounds the mounting holes 20 and fills the channels 32 and 34 in the frame 12. The mounting surface 44 also includes rectangular sections 56a and 58a positioned above and connected to the portions 56b and 58b that fill the channels 32 and 34. The first rectangular section 56a is adjacent to the first receiving section 46 and the second rectangular section 58a is adjacent to the second receiving section 48. As shown in FIGS. 3 and 4, the second rectangular section 58a is approximately 0.05 to 0.10 inches higher than the first rectangular section 56a.

Filling double channels 32 and 34 with injection molded elastomer militates against the delamination of the gasket 40 from the plastic frame member 12. The channels 32 and 34 provide a greater surface area for frictional gripping of the gasket 40 onto the frame member 12, and also provide physical obstructions to lateral dislocation of the gasket 40 relative to the frame 12. In less preferred embodiments, however, the complex retaining surface 40 and channels 32, 34 could be replaced with a single-channel construction or even flat frame and gasket surfaces which could be bonded together by, e.g., an adhesive. As mentioned above, the gasket 40 should "wet" the inner surface 30 of frame 12 for optimum light transmission.

FIG. 5 illustrates the license plate cover 10 relative to a license plate 60 and vehicle frame mounting bracket portions 100. The border 62 of the license plate contacts the compression ribs 46b and 48b. Conventional license plates are stamped or embossed to leave a raised central area 66 and a relatively depressed peripheral area 68, with a bevel or step 70 in between. The letters and numbers 72 of the vehicle license plate and other indicia are stamped into raised central area 66. The different elevations of ribs 46b and 48b allow them to respectively mate with the raised central area 66 and the depressed peripheral area 68. This improves the seal and prevents buckling or warping of the license plate by the cover 10. The stepped compression ribs 46b and 48b and the raised rim 52 of the gasket 40 provide a seal that protects the license plate and the fasteners that attach the license plate from damaging environmental elements.

In summary, a vehicle license plate cover has been described and illustrated which provides for a sealing engagement to a beveled license plate and a peripheral band of color that is protected from the elements. However, while the invention has been described with respect to the illustrated embodiment, it is not limited thereto, but only by the scope and spirit of the appended claims.

I claim:

1. Apparatus for mounting a vehicle license plate, comprising:
   a frame having a periphery, an outer side, an inner side for disposal adjacent a license plate and an elongated channel disposed near the periphery of the frame, the channel having a bottom and sides extending inwardly from the bottom of the channel toward the license plate, the frame including a transparent central area disposed laterally inwardly of the channel for viewing the license plate from the outer side of the frame; and
   an elongated annular thermoplastic elastomeric gasket injection molded onto the inner side of the frame near the periphery of the frame, to fill the channel and to adhere to the bottom and sides of the channel, the gasket forming a flat receiving surface facing the license plate, at least one elongate compression rib formed on the gasket adjacent the flat receiving surface to extend inwardly from the flat receiving surface toward the license plate, the rib laterally surrounding a majority of the central area of the frame, leaving a bottom portion open.

2. The apparatus of claim 1, wherein the frame further comprises a plurality of holes for receiving respective fasteners to a vehicle license plate mounting bracket, the gasket closely laterally surrounding the holes.

3. The apparatus of claim 1, wherein the inner side of the frame includes two elongate channels, the elastomeric gasket being molded into both said channels.

4. The apparatus of claim 1, wherein the gasket is colored, the gasket molecularly adhered or wetted to the inner side of the frame such that a band of color appears to a viewer from the outside of the frame, undiminished by any optical refraction or scattering which would have been caused by air gaps between the gasket and the inner side of the frame.

5. The apparatus of claim 1, wherein the gasket is formed of TEA.

6. Apparatus for mounting a license plate to a vehicle, comprising:
   a frame having a periphery, an outer side, and an inner side for disposal adjacent a license plate;
   an elongated elastomeric gasket disposed on the inner side near the frame periphery and having a generally planar receiving surface inwardly facing toward the license plate, the gasket further including at least one elongate compression rib which extends inwardly from said generally planar receiving surface to contact the license plate;
   a plurality of mounting fastener holes formed in the frame, each mounting fastener hole having a continuous sidewall, formed integrally with the frame, which extends from the outer side of the frame to the inner side of the frame, the gasket closely laterally surrounding the mounting fastener holes, the sidewall extending inwardly to be substantially coplanar with the generally planar receiving surface of the gasket, wherein the sidewalls of the mounting fastener holes prevent the fasteners from overcompressing the gasket and fracturing the frame.

7. The apparatus of claim 6, wherein the frame further includes a transparent central area disposed laterally inwardly of the fastener holes and gasket for viewing the license plate from the outer side of the frame.

8. The apparatus of claim 6, wherein each mounting fastener hole sidewall forms a step, a first length of the hole extending from the outer side of the frame to the step and sized to receive a head of a fastener, a second length of the hole extending from the step to the inner side of the frame and sized to receive a shank of the fastener but not the head thereof.

* * * * *